(12) United States Patent
Watanabe et al.

(10) Patent No.: US 6,288,064 B1
(45) Date of Patent: Sep. 11, 2001

(54) REMEDY FOR ERECTION FAILURE COMPRISING FUSED PYRIDAZINE COMPOUND

(75) Inventors: Nobuhisa Watanabe, Ibaraki (JP); Yasuhiro Kabasawa, London (GB); Shinya Abe, Ibaraki (JP); Mayu Shibazaki, Fukui (JP); Hiroki Ishihara, Ibaraki (JP); Kohtarou Kodama, Ibaraki (JP); Hideyuki Adachi, Ibaraki (JP)

(73) Assignee: Eisai Co., Ltd., Tokyo (JP)

( * ) Notice: Subject to any disclaimer, the term of this patent is extended or adjusted under 35 U.S.C. 154(b) by 0 days.

(21) Appl. No.: 09/202,422

(22) PCT Filed: Aug. 8, 1997

(86) PCT No.: PCT/JP97/02785

§ 371 Date: Feb. 16, 1999

§ 102(e) Date: Feb. 16, 1999

(87) PCT Pub. No.: WO98/07430

PCT Pub. Date: Feb. 26, 1998

(30) Foreign Application Priority Data

Aug. 20, 1996  (JP) .................................................. 8218204

(51) Int. Cl.[7] ......................... A61K 31/50; A61K 31/495; A61K 31/535
(52) U.S. Cl. ........................ 514/248; 514/252; 514/253; 514/234.5
(58) Field of Search ................................... 514/248, 252, 514/253, 234.5

(56) References Cited

U.S. PATENT DOCUMENTS 5,849,741 * 12/1998 Watanabe et al. ................... 514/248

FOREIGN PATENT DOCUMENTS

| 468789A2 | 1/1992 | (EP) . |
| 722936A1 | 7/1996 | (EP) . |
| 6-56831 | 3/1994 | (JP) . |
| 8-143558 | 6/1996 | (JP) . |
| 9605176 | 2/1996 | (WO) . |
| 96/16644 | * 6/1996 | (WO) ............................ A61K/31/00 |

OTHER PUBLICATIONS

Jabob Rajfer et al, The New England Journal of Medicine, Jan. 9, 1992, pp. 90–94.

Peggy A. Bush et al, The Journal of Urology vol. 147, 1650–1655, Jun. 1992.

Peggy A. Bush et al, Int'l. J. Impotence Res. (1992) 4, 85–93.

Anne Bowman et al, Br. J. Pharmac (1984), 81, 665–674.

* cited by examiner

*Primary Examiner*—Russell Travers
*Assistant Examiner*—Shengjun Wang
(74) *Attorney, Agent, or Firm*—Birch, Stewart, Kolasch & Birch, LLP

(57) ABSTRACT

The present invnetion provides a remedy for erectile dysfunction. The active ingredient thereof is a fused pyridazine compound represented by the following formula (I) or a pharmacologically acceptable salt thereof:

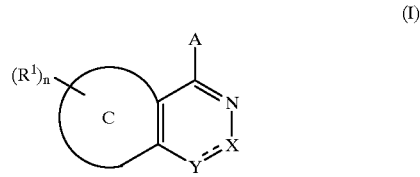

(wherein the ring C represents a 5 or 6 membered ring optionally having hetero atom(s); n is an integer of from 1 to 4; $R^1$ represents a hydrogen, a halogen, a cyano, etc.; A represents a hydrogen, a halogen, an optionally substituted amino, etc.; X represents a group represented by the formula —N═, etc.; and Y represents the formula —CO—, an optionally substituted amino, etc).

12 Claims, No Drawings

REMEDY FOR ERECTION FAILURE COMPRISING FUSED PYRIDAZINE COMPOUND

This application is the national phase under 35 U.S.C. §371 of prior PCT International Application No. PCT/JP97/02785 which has an International filing date of Aug. 8, 1997 which designated the United States of America.

BACKGROUND OF THE INVENTION

1. Technical Field

The present invention relates to remedies for erectile dysfunction which contain as the active ingredient novel fused pyridazine compounds.

2. Prior Art

It is said that the number of latent patients with erectile dysfunction amounts to about 3,000,000 in Japan. In U.S.A., it is reported that the number of patients with erectile dysfunction reaches 20,000,000 and 15% of males in the fifties and about ⅓ of those in the sixties suffer from this disease. In this aging society, sexual intercourse is regarded as a pleasant and emotional behavior. With the needs for the improved quality of life, it is anticipated that erectile dysfunction will raise not only a medical problem but also a social problem in future. This disease is classified into organic impotence caused by disorders in the nerves, blood vessels or muscles in the penis per se or sexual hormones and functional (psychic) impotence caused by mental or psychologic troubles. There are three factors necessary for erection, i.e., an increase in the penile arterial blood flow, the regulation of blood leakage from the penile veins, and the relaxation of the cavernous tissue. Erectile dysfunction arises when at least one of these conditions is inhibited.

The urological treatments for erectile dysfunction effected today involve drug therapy and operative penile prosthesis with the use of penile prosthetic appliances.

As the drug therapy, it is possible to inject papaverine hydrochloride or prostaglandin E1 into the penile cavernous tissue. However, this treatment is scarcely performed today, since it is not allowed in Japan that a patient gives an injection to himself and it is impossible in practice to go for a doctor every time he has coitus. In addition, the injection of papaverine hydrochloride would cause, though exceptionally, a painful symptom called priapism. Thus, the treatments with the existing drugs are not practically usable. Accordingly, it has been urgently desired to develop a drug therapy therefor which is clinically efficacious in practice.

In 1984, Bowman and Drummond reported that a selective cyclic GMP phosphodiesterase inhibitor M&B22948 (zaprinast) increased cyclic GMP in the tissue and relaxed the bovine retractor penis muscle (Cyclic GMP mediates neurogenic relaxation in the bovine retractor penis muscle, Br. J. Pharmacol., RI, 665–674, 1984). Subsequently, other workers have reported one after another the relaxation of the penis cavernosum by increasing cyclic GMP in the tissue (Int. J. Impotence Res., 4, 85–93, 1992; J. Urol., 147, 1650–1655, 1992; and N. Engl. J. Med., 32S, 90–94, 1992). However, none of the compounds employed in these studies can be satisfactorily employed clinically due to poor efficacy, etc.

DISCLOSURE OF THE INVENTION

Under these circumstances, the present inventors have conducted extensive studies and consequently found out that fused pyridazine compounds represented by the formula (I), which are disclosed in WO96/05176 show a high selectivity for phosphodiesterase type v which is an enzyme capable of degrading cyclic GMP and a potent inhibitory effect, thus completing the present invention:

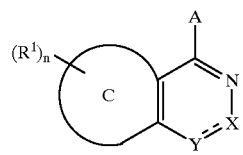

(I)

(wherein the ring C represents an unsaturated 5 or 6 membered ring optionally having hetero atom(s); n is 0 or an integer of from 1 to 4; $R^1$ represents a halogen, an optionally substituted lower alkyl, an optionally substituted lower alkoxy, an optionally substituted cycloalkyl, a nitro, a cyano, a group represented by the formula —$NR^2R^3$ (wherein $R^2$ and $R^3$ are the same as or different from each other and represent a hydrogen, an optionally substituted lower alkyl, an acyl, an optionally substituted arylalkyl or an optionally substituted heteroarylalkyl, or $R^2$ and $R^3$ together with the nitrogen atom to which they are bonded may form a ring, and the ring may be substituted), a group represented by the formula —O—$R^9$ (wherein $R^9$ represents a hydrogen, an optionally substituted lower alkyl, an acyl, an optionally substituted arylalkyl or an optionally substituted heteroarylalkyl), a group represented by the formula —S—$R^{10}$ (wherein $R^{10}$ represents a hydrogen, an optionally substituted lower alkyl, an acyl, an optionally substituted arylalkyl, or an optionally substituted heteroarylalkyl), a group represented by the formula;

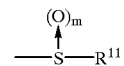

(wherein $R^{11}$ represents a hydrogen, a lower alkyl or an amino; and m is 0 or an integer of 1 or 2) or an optionally protected carboxy, provided that when n is 2 to 4, then $R^1$'s may independently represent the above substituents;

A represents a hydrogen, a halogen, a group represented by the formula —$NR^4R^5$ (wherein $R^4$ and $R^5$ are the same as or different from each other and represent a hydrogen, an optionally substituted lower alkyl, an acyl, an optionally substituted arylalkyl or an optionally substituted heteroarylalkyl, or $R^4$ and $R^5$ together with the nitrogen atom to which they are bonded may form a ring, and the ring may be substituted), an optionally substituted aryl, an optionally substituted heteroaryl, an optionally substituted arylalkyl or an optionally substituted heteroarylalkyl;

X represents a group represented by the formula —$NR^6$— (wherein $R^6$ represents a hydrogen, an optionally substituted lower alkyl, an optionally substituted arylalkyl or an optionally substituted heteroarylalkyl) or a group represented by the formula —N=;

Y represents a group represented by the formula —CO— or —C(B)= [wherein B represents a hydrogen, a halogen, a group represented by the formula —$NR^7R^8$ (wherein $R^7$ and $R^8$ are the same as or different from each other and represent a hydrogen, an optionally substituted lower alkyl, an acyl, an optionally substituted arylalkyl or an optionally substituted heteroarylalkyl, or $R^7$ and $R^8$ together with the nitrogen atom to which they are bonded may form a ring, and the ring may be substituted), a group represented by the formula —O—$R^{12}$ (wherein $R^{12}$ represents a hydrogen, an optionally substituted lower alkyl, an acyl, an optionally substituted arylalkyl or an optionally substituted heteroarylalkyl), —S—$R^{13}$ (wherein $R^{13}$ represents a hydrogen, an optionally substituted lower alkyl, an acyl, an optionally substituted arylalkyl or an optionally substituted heteroarylalkyl), an optionally substituted aryl, an optionally substituted heteroaryl, an optionally substituted arylalkyl or an optionally substituted heteroarylalkyl]; and represents a double or single bond; provided that when the ring C is a benzene ring, then the case where n is 0 is excluded}.

In addition to the remedies (1) as described above, the present invention further provides: (2) remedies for female sexual dysfunction, dysmenorrhea or premature birth comprising as the active ingredient the above fused pyridazine compounds or pharmacologically acceptable salts thereof; (3) medicinal compositions comprising a therapeutically effective dose of the above fused pyridazine compounds or pharmacologically acceptable salts thereof and pharmacologically acceptable carriers; (4) a method for treating erectile dysfunction, female sexual dysfunction, dysmenorrhea or premature birth which comprises administering a therapeutically effective dose of the above fused pyridazine compounds or pharmacologically acceptable salts thereof to a patient with erectile dysfunction, female sexual dysfunction or dysmenorrhea or a patient giving premature birth; and (5) use of the above fused pyridazine compounds or pharmacologically acceptable salts thereof for producing remedies for erectile dysfunction, female sexual dysfunction, dysmenorrhea or premature birth.

In the definition given herein, as the unsaturated 5 or 6 membered ring optionally having hetero atom(s) represented by the ring C, benzene, pyridine, pyrazine, pyrimidine, pyridazine, pyrrole, imidazole, pyrazole, thiophene and furan rings may be proposed.

In the definition represented by the above formula (I), the lower alkyl in the "optionally substituted lower alkyl" as used in the definition of $R^1$, $R^{1a}$, $R^{1b}$, $R^2$, $R^3$, $R^4$, $R^5$, $R^6$, $R^7$, $R^8$, $R^9$, $R^{10}$, $R^{11}$, $R^{12}$ and $R^{13}$ means linear or branched $C_{1-6}$ alkyl such as methyl, ethyl, n-propyl, isopropyl, n-butyl, isobutyl, 1-methylpropyl, tert-butyl, n-pentyl, 1-ethylpropyl, isoamyl and n-hexyl. Examples of the substituent include hydroxy, nitro, amino, cyano, acyl such as acetyl and benzoyl, lower alkoxy such as methoxy and ethoxy, halogeno such as fluorine, chlorine, bromine and iodine and optionally protected carboxy. Either one or more of these substituents may be attached to one or more carbon atoms in the lower alkyl.

The lower alkoxy in the "optionally substituted lower alkoxy" as used in the definition of $R^1$, $R^{1a}$ and $R^{1b}$ means those derived from the above-mentioned lower alkyl, for example, methoxy, ethoxy and propoxy. Examples of the substituent include hydroxy, nitro, amino, cyano, acyl such as acetyl and benzoyl, lower alkoxy such as methoxy and ethoxy, halogeno such as fluorine, chlorine, bromine and iodine, and optionally protected carboxy. Either one or more of these substituents may be attached to one or more carbon atoms in the lower alkoxy.

The cycloalkyl in the "optionally substituted cycloalkyl" as used in the definition of $R^1$, $R^{1a}$ and $R^{1b}$ means $C_{3-8}$ ones. Examples of the substituent include hydroxy, nitro, amino, cyano, acyl such as acetyl and benzoyl, lower alkoxy such as methoxy and ethoxy, halogeno such as fluorine, bromine and iodine, and optionally protected carboxy. Either one or more of these substituents may be attached to one or more carbon atoms in the cycloalkyl.

The term "acyl" as used in the definition of $R^2$, $R^3$, $R^4$, $R^5$, $R^6$, $R^7$, $R^8$, $R^9$, $R^{10}$, $R^{12}$, and $R^{13}$ means acyl derived from aliphatic, aromatic or heterocyclic groups. Examples thereof include lower alkanoyl such as formyl, acetyl, propionyl, butyryl, valeryl, isovaleryl and pivaloyl, aroyl such as benzoyl, toluoyl and naphthoyl, and heteroaroyl such as furoyl, nicotinoyl and isonicotinoyl. Namely, any groups derived from various carboxylic acids are involved therein. Among these substituents, it is preferable to use formyl, acetyl, benzoyl, etc.

The aryl in the "optionally substituted aryl" as used in the definition of A and B means those derived from aromatic rings such as phenyl, 1-naphthyl, 2-naphthyl and anthracenyl. Examples of the substituent include hydroxy, nitro, amino, cyano, acyl such as acetyl and benzoyl, lower alkoxy such as methoxy and ethoxy, halogeno such as fluorine, chlorine, bromine and iodine, and optionally protected carboxy.

The heteroaryl in the "optionally substituted heteroarylalkyl" as used in the definition of A and B means monocyclic or heterocyclic groups containing one or more atoms of nitrogen, sulfur, oxygen, etc. Examples thereof include pyridyl, pyrrolyl, imidazolyl, pyrazolyl, pyrazyl, pyrimidyl, pyridazyl, thienyl, pyranyl, isothiazolyl, isoxazolyl, furazanyl, benzothienyl, furyl, indolyl, indolizinyl, isoindolyl, benzothiazolyl, benzimidazolyl and quinazolyl. Examples of the substituent include hydroxy, nitro, amino, cyano, acyl such as acetyl and benzoyl, lower alkoxy such as methoxy and ethoxy, halogeno such as fluorine, chlorine, bromine and iodine, and optionally protected carboxy.

The expression "$R^2$ and $R^3$, $R^4$ and $R^5$, or $R^7$ and $R^8$ together with the nitrogen atom to which they are bonded may form a ring" as used in the definition of —$NR^2R^3$ in $R^1$, —$NR^4R^5$ in A and —$NR^7R^8$ in B means that $R^2$ and $R^3$, $R^4$ and $R^5$, or $R^7$ and $R^8$ may form, together with the nitrogen atom to which they are bonded, for example, piperidinyl, pyrrolidinyl, piperazinyl, etc. Examples of the substituent include hydroxy, optionally substitutedamino, aminoalkyl, nitro, nitroalkyl, loweralkoxy, lower alkoxyalkyl, hydroxyalkyl, optionally protected carboxy and optionally protected carboxyalkyl. The most preferable examples of the substituent include hydroxy, hydroxymethyl, hydroxyethyl, carboxymethyl and carboxyethyl.

The aryl in the "optionally substituted arylalkyl" as used in the definition of $R^2$, $R^3$, $R^4$, $R^5$, $R^6$, $R^7$, $R^8$, $R^9$, $R^{10}$, $R^{12}$, $R^{13}$ and Y means those derived from aromatic rings such as phenyl, 1-naphthyl, 2-naphthyl and anthracenyl. The alkyl as used herein means those derived from the above-mentioned lower alkyl. Examples of the substituent include hydroxy, nitro, amino, cyano, acyl such as acetyl and benzoyl, lower alkoxy such as methoxy and ethoxy, halogeno such as fluorine, chlorine, bromine and iodine, and optionally protected carboxy.

The heteroaryl in the "optionally substituted heteroarylalkyl" as used in the definition of $R^2$, $R^3$, $R^4$, $R^5$, $R^6$, $R^7$, $R^8$, $R^9$, $R^{10}$, $R^{12}$, $R^{13}$ and Y means monocyclic or heterocyclic groups containing one or more atoms of nitrogen, sulfur, oxygen, etc. Examples thereof include pyridyl, pyrrolyl, imidazolyl, pyrazolyl, pyrazyl, pyrimidyl, pyridazyl, thienyl, pyranyl, isothiazolyl, isoxazolyl, furazanyl, benzothienyl, furyl, indolyl, indolizinyl, isoindolyl, benzothiazolyl, benzimidazolyl and quinazolyl. The alkyl as used herein manes those derived from the above-mentioned lower alkyl. Examples of the substituent include hydroxy, nitro, amino, cyano, acyl such as acetyl and benzoyl, lower alkoxy such as methoxy and ethoxy, halogeno such as fluorine, chlorine, bromine and iodine, and optionally protected carboxy.

The term "halogeno" as used in the definition of $R^1$, $R^{1a}$, $R^{1b}$, $R^{12}$, $R^{13}$ and $R^{14}$ means fluorine, chlorine, bromine, iodine, etc.

Examples of the pharmacologically acceptable salts to be used in the present invention include inorganic acid salts such as hydrochlorides, sulfates, hydrobromides and phosphates and organic acid salts such as formates, acetates, trifluoroacetates, maleates, fumarates, tartrates, methanesulfonates, benzenesulfonates and toluenesulfonates.

Some of the compounds according to the present invention form hydrates. Needless to say, these hydrates are also included within the scope of the present invention.

Among the compounds according to the present invention, preferable ones are fused pyridazine compounds represented by the following formula (I) wherein the ring C is benzene or pharmacologically acceptable salts thereof:

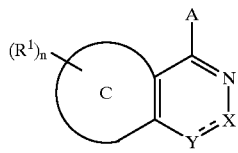

(I)

(wherein n, $R^1$, A, X, Y and

----- are each as defined above).

Among them, still preferable ones are fused pyridazine compounds represented by the following formula (IV) or pharmacologically acceptable salts thereof:

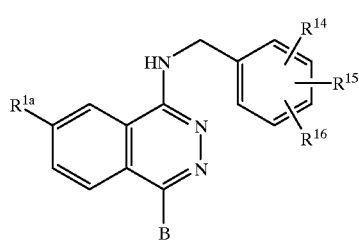

(IV)

(wherein B, $R^{1a}$, $R^{14}$, $R^{15}$ and $R^{16}$ are each as defined above).

Because of being excellent in oral absorbability and long-lasting action, these fused pyridazine compounds or pharmacologically acceptable salts thereof can be percutaneously, intravenously or orally administered for treatment without resort to injection directly into the penile cavernosum, which makes them favorable as remedies for erectile dysfunction.

Although the compounds of the present invention may be administered in an arbitrary dose without restriction, they are usually given to an adult in a dose of from 5 $\mu$g to 100 mg, preferably from 10 to 1,000 $\mu$g, in the case of intravenous administration, or in a dose of from 1 to 1,000 mg, preferably from 5 to 100 mg, in the case of oral administration.

WO96/05176 discloses processes for producing these fused pyridazine compounds or pharmacologically acceptable salts thereof and their phosphodiesterase type V inhibitory activities.

Although the compounds of the present invention aim at treating male erectile dysfunction, these compounds are also efficacious against female sexual dysfunction, premature birth and dysmenorrhea.

Best Mode for Carrying Out the Invention:

The following Examples will be given to show the effects of the compounds of the present invention.

EXAMPLE

Relaxing Effect on Extirpated Rabbit Penile Cavernosum Preparation

The penis was extirpated from a Japanese white rabbit (about 3 kg) under anesthesia with pentobarbital (50 mg/kg) administered intravenously to give a penile cavernosum preparation (about 20×1.5×1.5 mm). This preparation was suspended in a Magnus tube filled up with Krebs-Henseleit's nutritive solution (containing 1 PM of indomethacin) at 37° C. and a gas mixture (95% oxygen +5% carbon dioxide) was bubbled thereinto. Then the isometric tension was recorded under a load of 2 g. To stabilize the contraction, contraction caused by adding a potassium chloride solution (final concentration: 50 mM) and washing with the nutritive solution were repeated for two times. Next, the preparation was contracted by adding a phenylephrine solution (final concentration: 10 $\mu$M). When the contraction was stabilized, 4-(3-chloro-4-methoxybenzyl)amino-6-cyano-1-(4-hydroxypiperidino)-phthalazine hydrochloride (hereinafter referred to as the compound A) was added cumulatively at a common ratio of 10 from 1 nM to 100 $\mu$M in the final concentration and the tension was continuously recorded. From the dose-response curve thus formed, the medium relaxation concentration of the compound A on the contraction was determined. The value obtained from six preparations was 4.47 $\mu$M (95% confidence limit: 1.88–10.6 $\mu$M)

TABLE 1

| Conc. ($\mu$M) of Compound A | Relaxation ratio (%) |
| --- | --- |
| 0.01 | 17.4 ± 1.4 |
| 0.1 | 28.1 ± 5.1 |
| 1.0 | 40.8 ± 10.4 |
| 10.0 | 61.4 ± 5.1 |
| 100.0 | 90.6 ± 1.6 |

PRODUCTION EXAMPLE 4-(3-Chloro-4-methoxybenzyl)amino-6-cyano-1-(4-hydroxypiperidino)phthalazine Hydrochloride 69 g of 6-cyano-2,3-dihydro-1,4-phthaladinedione was suspended in 400 ml of phosphorus oxychloride. After adding 75 ml of diisopropylethylamine, the mixture was heated under reflux for 40 minutes. Then the excessive phosphorus oxychloride was evaporated and the residue was dissolved in methylene chloride and poured into ice water. After filtering off the unnecessary through celite, the celite filter was washed with methylene chloride. The filtrate was extracted with methylene chloride. The organic layer was washed with a saturated aqueous solution of sodium bicarbonate, dilute hydrochloric acid and brine and dried over anhydrous magnesium sulfate. This solution was filtered by using silica gel and the solvent was evaporated to give 66 g of 6-cyano-1,4 -dichlorophthalazine as a pale orange solid.

$^1$H-NMR(400 MHz, CDCl$_3$) δ: 8.24(1H, dd, J=8.5, 1.5 Hz), 8.47(1H, dd, J=8.5, 1.0 Hz), 8.68(1H, dd, J=1.5, 1.0 Hz).

66.2 g of 6-cyano-1,4-dichlorophthalazine and 92 g of 3-chloro-4-methoxybenzylamine were suspended in 1,200 ml of tetrahydrofuran. After adding 250 ml of triethylamine, the resulting mixture was heated under reflux for 6 hours. The resulting crystals were filtered off and the filtrate was evaporated. The residue was purified by silica gel column chromatography (toluene:tetrahydrofuran=10:1) to give 59 g of 1-chloro-4-(3-chloro-4-methoxybenzyl)amino-6-cyanophthalazine as pale yellow crystals. M.p.: 213.0–214.5° C., Mass 359(MH+), $^1$H-NMR(400 MHz, CDCl$_3$) δ: 3.87(3H, s), 4.78(2H, d, J=5.0 Hz), 5.75(1H, t, J=5.0 Hz), 6.87(1H, d, J=8.5 Hz), 7.31(1H, dd, J=8.5, 2.0 Hz), 7.43(1H, d, J=2.0 Hz), 8.05(1H, dd, J=8.5, 1.5 Hz), 8.24(1H, dd, J=1.5, 1.0 Hz), 8.29(1H, dd, J=8.5, 0.5 Hz). 10.0 g of 1-chloro-4-(3-chloro-4-methoxybenzyl)amino-6-cyanophthalazine was dissolved in 50 ml of N-methyl-2-piperidone. After adding 43.32 g of 4-hydroxypiperidine and 10 ml of diisopropylethylamine, the resulting mixture was heated at 170° C. for 8 hours. Then ethyl acetate wag added thereto and the resulting mixture was successively washed for three times with water and once with brine and dried over anhydrous magnesium sulfate. After evaporating the solvent, the residue was purified by silica gel column chromatography (methylene chloride:methanol=30:1) to give 10.1 g of 4-(3-chloro-4-methoxybenzyl)amino-6-cyano-1-(4-hydroxypiperidino)phthalazine as yellow crystals. M.p.: 172.0–173.5° C., Mass 424(MH+), $^1$H-NMR(400 MHz, CDCl$_3$) δ: 1.70(1H, brs), 1.80–1.90 (2H, m), 2.07–2.15(2H, m), 3.05–3.15(2H, m), 3.50–3.60 (2H, m), 3.87(3H, s), 3.90–4.00(1H, m), 4.74(2H, d, J=5.0 Hz), 5.41(1H, t, J=5.0 Hz), 6.87(1H, d, J=8.5 Hz), 7.29(1H, dd, J=8.5, 2.0 Hz), 7.42(1H, d, J=2.0 Hz), 7.95(1H, dd, J=8.5, 1.5 Hz), 8.12(1H, dd, J=1.5, 1.0 Hz), 8.21(1H, dd, J=8.5, 0.5 Hz).

10.8 g of 4-(3-chloro-4-methoxybenzyl)amino-6-cyano-1-(4-hydroxypiperidino)phthalazine was suspended in a mixture of ethanol (60 ml) with water (30 ml) and 30 ml of a 1 N aqueous solution of hydrochloric acid was added thereto. After dissolving by heating once, the mixture was cooled by allowing to stand at room temperature. The resulting crystals were collected by filtration and hot air-dried at 80° C. overnight to give 9.37 g of the title compound as yellow crystals. M.p. 217–227° C. (decomp.), Mass 424 (MH+), $^1$H-NMR(400 MHz, CDCl$_3$) δ: 1.61–1.70(2H, m), 1.90–1.97(2H, m), 2.97–3.04(2H, m), 3.37–3.48(2H, m), 3.70–3.79(1H, m), 3.84(3H, s), 4.70(2H, d, J=5.5 Hz), 7.15(1H, d, J=8.5 Hz), 7.44(1H, dd, J=8.5, 2.0 Hz), 7.59(1H, d, J=2.0 Hz), 8.23(1H, dd, J=8.5 Hz), 8.45(1H, d, J=8.5 Hz), 9.33(1H, s), 10.10(1H, brs), 14.00(1H, brs)

What is claimed is:

1. A method for treating erectile dysfunction which comprises administering an effective amount of a fused pyridazine compound represented by the following formula (I) or a pharmacologically acceptable salt thereof, to a patient in need thereof:

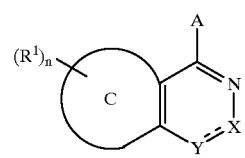

(I)

wherein the ring C represents an unsaturated 5 or 6 membered ring optionally having one heteroatom;

n is 0 or an integer of from 1 to 4;

$R^1$ represents a halogen, an optionally substituted lower alkyl, an optionally substituted lower alkoxy, an optionally substituted cycloalkyl, a nitro, a cyano, a group represented by the formula —$NR^2R^3$, wherein $R^2$ and $R^3$ are the same as or different from each other and represent a hydrogen, an optionally substituted lower alkyl, an acyl, an optionally substituted arylalkyl or an optionally substituted heteroarylalkyl, or $R^2$ and $R^3$ together with the nitrogen atom to which they are bonded may form a ring, and the ring may be substituted, a group represented by the formula —O—$R^9$, wherein $R^9$ represents a hydrogen, an optionally substituted lower alkyl, acyl, an optionally substituted arylalkyl or an optionally substituted heteroarylalkyl, a group represented by the formula —S—$R^{10}$, wherein $R^{10}$ represents a hydrogen, an optionally substituted lower alkyl, acyl, an optionally substituted arylalkyl or an optionally substituted heteroarylalkyl, a group represented by the formula:

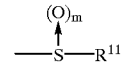

wherein $R^{11}$ represents a hydrogen, a lower alkyl or an amino; and m is 0 or an integer of 1 or 2, or an optionally protected carboxy, provided that when n is 2 to 4, then $R^1$s may independently represent the above substituents;

A represents a hydrogen, a halogen, a group represented by the formula —$NR^4R^5$, wherein $R^4$ and $R^5$ are the same as or different from each other and represent a hydrogen, an optionally substituted lower alkyl, an acyl, an optionally substituted arylalkyl or an optionally substituted heteroarylalkyl, or $R^4$ and $R^5$ together with the nitrogen atom to which they are bonded may form a ring, and the ring may be substituted, an optionally substituted aryl, an optionally substituted heteroaryl, an optionally substituted arylalkyl or an optionally substituted heteroarylalkyl;

X represents a group represented by the formula —$NR^6$—, wherein $R^6$ represents a hydrogen, an optionally substituted lower alkyl, an optionally substituted arylalkyl or an optionally substituted heteroarylalkyl or a group represented by the formula —N═;

Y represents a group represented by the formula —CO— or —C(B)═, wherein B represents a hydrogen, a halogen, a group represented by the formula —$NR^7R^8$, wherein $R^7$ and $R^8$ are the same as or different from each other and represent a hydrogen, an optionally substituted lower alkyl, an acyl, an optionally substituted arylalkyl or an optionally substituted heteroarylalkyl, or $R^7$ and $R^8$ together with the nitrogen atom to which they are bonded may form a ring, and the ring may be substituted, a group represented by the formula —O—$R^{12}$,
wherein $R^{12}$ represents a hydrogen, an optionally substituted lower alkyl, an acyl, an optionally substituted arylalkyl or an optionally substituted heteroarylalkyl, a group represented by the formula —S—$R^{13}$,
wherein $R^{13}$ represents a hydrogen, an optionally substituted lower alkyl, an acyl, an optionally substituted arylalkyl or an optionally substituted heteroarylalkyl, an optionally substituted aryl, an optionally substituted heteroaryl, an optionally substituted arylalkyl or an optionally substituted heteroarylalkyl; and

==== represents a double or single bond;
provided that when C is a benzene ring, then the case where n is 0 is excluded.

2. The method as set forth in claim 1, wherein the ring C is a benzene ring.

3. The method as set forth in claim 1, wherein X is nitrogen and Y is the formula —C(B)=,
wherein B represents a hydrogen, a halogen, a group represented by the formula —$NR^7R^8$,
wherein $R^7$ and $R^8$ are the same as or different from each other and represent a hydrogen, an optionally substituted lower alkyl, an acyl, an optionally substituted arylalkyl or an optionally substituted heteroarylalkyl, or $R^7$ and $R^8$ together with the nitrogen atom to which they are bonded may form a ring, and the ring may be substituted, a group represented by the formula —O—$R^{12}$,
wherein $R^{12}$ represents a hydrogen, an optionally substituted lower alkyl, an acyl, an optionally substituted arylalkyl or an optionally substituted heteroarylalkyl, a group represented by the formula —S—$R^{13}$,
wherein $R^{13}$ represents a hydrogen, an optionally substituted lower alkyl, an acyl, an optionally substituted arylalkyl or an optionally substituted heteroarylalkyl, an optionally substituted aryl, an optionally substituted heteroaryl, an optionally substituted arylalkyl or an optionally substituted heteroarylalkyl.

4. The method as set forth in claim 1, wherein the ring C is a pyridine ring, X is nitrogen and Y is the formula —C(B)=wherein B represents a hydrogen, a halogen, a group represented by the formula —$NR^7R^8$,
wherein $R^7$ and $R^8$ are the same as or different from each other and represent a hydrogen, an optionally substituted lower alkyl, an acyl, an optionally substituted arylalkyl or an optionally substituted heteroarylalkyl, or $R^7$ and $R^8$ together with the nitrogen atom to which they are bonded may form a ring, and the ring may be substituted, a group represented by the formula —O—$R^{12}$,
wherein $R^{12}$ represents a hydrogen, an optionally substituted lower alkyl, an acyl, an optionally substituted arylalkyl or an optionally substituted heteroarylalkyl, a group represented by the formula —S—$R^{13}$,
wherein $R^{13}$ represents a hydrogen, an optionally substituted lower alkyl, an acyl, an optionally substituted arylalkyl or an optionally substituted heteroarylalkyl, an optionally substituted aryl, an optionally substituted heteroaryl, an optionally substituted arylalkyl or an optionally substituted heteroarylalkyl.

5. The method as set forth in claim 1 or 2, wherein the fused pyridazine compound is represented by the following formula (II):

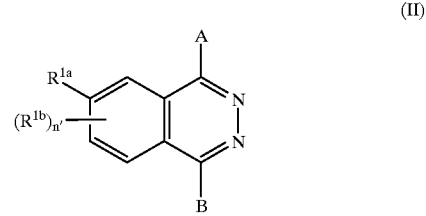

(II)

wherein $R^{1a}$ and $R^{1b}$ are different from each other and each represents a halogen, an optionally substituted lower alkyl, an optionally substituted lower alkoxy, an optionally substituted cycloalkyl, a nitro, a cyano or a group represented by the formula —$NR^2R^3$,
wherein $R^2$ and $R^3$ are the same as or different from each other and represent a hydrogen, an optionally substituted lower alkyl, an acyl, an optionally substituted arylalkyl or an optionally substituted heteroarylalkyl, or $R^2$ and $R^3$ together with the nitrogen atom to which they are bonded may form a ring, and the ring may be substituted;

n is 0 or an integer from 1 to 3;

A represents a hydrogen, a halogen, a group represented by the formula —$NR^4R^5$,
wherein $R^4$ and $R^5$ are the same as or different from each other and represent a hydrogen, an optionally substituted lower alkyl, an acyl, an optionally substituted arylalkyl or an optionally substituted heteroarylalkyl, or $R^4$ and $R^5$ together with the nitrogen atom to which they are bonded may form a ring, and the ring may be substituted, an optionally substituted aryl, an optionally substituted heteroaryl, an optionally substituted arylalkyl or an optionally substituted heteroarylalkyl and B represents a hydrogen, a halogen, a group represented by the formula —$NR^7R^8$,
wherein $R^7$ and $R^8$ are the same as or different from each other and represent a hydrogen, an optionally substituted lower alkyl, an acyl, an optionally substituted arylalkyl or an optionally substituted heteroarylalkyl, or $R^7$ and $R^8$ together with the nitrogen atom to which they are bonded may form a ring, and the ring may be substituted, a group represented by the formula —O—$R^{12}$,
wherein $R^{12}$ represents a hydrogen, an optionally substituted lower alkyl, an acyl, an optionally substituted arylalkyl or an optionally substituted heteroarylalkyl, a group represented by the formula —S—$R^{13}$,
wherein $R^{13}$ represents a hydrogen, an optionally substituted lower alkyl, an acyl, an optionally substituted arylalkyl or an optionally substituted heteroarylalkyl, an optionally substituted aryl, an optionally substituted heteroaryl, an optionally substituted arylalkyl or an optionally substituted heteroarylalkyl.

6. The method as set forth in claim 1 or 2, wherein the fused pyridazine compound is represented by the following formula (III):

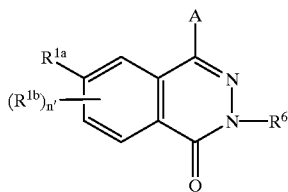

(III)

wherein R$^{1a}$ and R$^{1b}$ are different from each other and represent a halogen, an optionally substituted lower alkyl, an optionally substituted lower alkoxy, an optionally substituted cycloalkyl, a nitro, a cyano or a group represented by the formula —NR$^2$R$^3$, wherein R$^2$ and R$^3$ are the same as or different from each other and represent a hydrogen, an optionally substituted lower alkyl group, an acyl, an optionally substituted arylalkyl or an optionally substituted heteroarylalkyl, or R$^2$ and R$^3$ together with the nitrogen atom to which they are bonded may form a ring, and the ring may be substituted;

R$^6$ represents a hydrogen, an optionally substituted lower alkyl, an optionally substituted arylalkyl or an optionally substituted heteroarylalkyl;

n' is 0 or an integer of 1 to 3;

A represents a hydrogen, a halogen, a group represented by the formula —NR$^4$R$^5$, wherein R$^4$ and R$^5$ are the same as or different from each other and represent a hydrogen, an optionally substituted lower alkyl, an acyl, an optionally substituted arylalkyl or an optionally substituted heteroarylalkyl, or R$^4$ and R$^5$ together with the nitrogen atom to which they are bonded may form a ring, and the ring may be substituted, an optionally substituted aryl, an optionally substituted heteroaryl, an optionally substituted arylalkyl or an optionally substituted heteroarylalkyl.

7. The method as set forth in claim 1, wherein the fused pyridazine compound is represented by the following formula (IV):

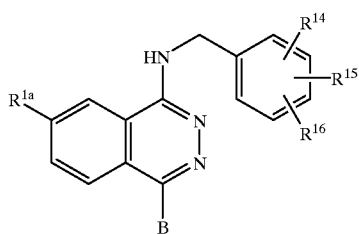

(IV)

wherein R$^{14}$, R$^{15}$ and R$^{16}$ are the same as or different from each other and represent a hydrogen, a halogen, an optionally substituted lower alkyl or an optionally substituted lower alkoxy, or two of R$^{14}$, R$^{15}$ and R$^{16}$ bonded to carbon atoms adjacent to each other may form methylenedioxy or ethylenedioxy;

R$^{1a}$ represents a halogen, an optionally substituted lower alkyl, an optionally substituted lower alkoxy, an optionally substituted cycloalkyl, a nitro, a cyano or a group represented by the formula —NR$^2$R$^3$, wherein R$^2$ and R$^3$ are the same as or different from each other and represent a hydrogen, an optionally substituted lower alkyl, an acyl, an optionally substituted arylalkyl or an optionally substituted heteroarylalkyl, or R$^2$ and R$^3$ together with the nitrogen atom to which they are bonded may form a ring, and the ring may be substituted and B represents a hydrogen, a halogen, a group represented by the formula —NR$^7$R$^8$, wherein R$^7$ and R$^8$ are the same as or different from each other and represent a hydrogen, an optionally substituted lower alkyl, an acyl, an optionally substituted arylalkyl or an optionally substituted heteroarylalkyl, or R$^7$ and R$^8$ together with the nitrogen atom to which they are bonded may form a ring, and the ring may be substituted, a group represented by the formula —O—R$^{12}$, wherein R$^{12}$ represents a hydrogen, an optionally substituted lower alkyl, an acyl, an optionally substituted arylalkyl or an optionally substituted heteroarylalkyl, a group represented by the formula —S—R$^{13}$, wherein R$^{13}$ represents a hydrogen, an optionally substituted lower alkyl, an acyl, an optionally substituted arylalkyl or an optionally substituted heteroarylalkyl, an optionally substituted aryl, an optionally substituted heteroaryl, an optionally substituted arylalkyl or an optionally substituted heteroarylalkyl.

8. The method as set forth in claim 1, wherein the fused pyridazine compound is represented by the following formula (V):

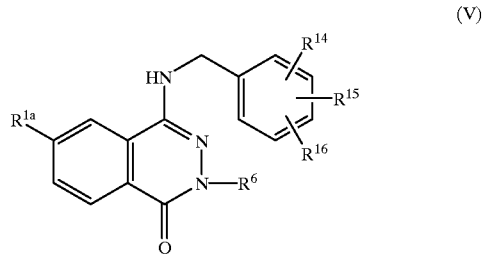

(V)

wherein R$^{1a}$ represents a halogen, an optionally substituted lower alkyl, an optionally substituted lower alkoxy, an optionally substituted cycloalkyl, a nitro, a cyano or a group represented by the formula —NR$^2$R$^3$, wherein R$^2$ and R$^3$ are the same as or different from each other and represent a hydrogen, an optionally substituted lower alkyl, an acyl, an optionally substituted arylalkyl or an optionally substituted heteroarylalkyl, or R$^2$ and R$^3$ together with the nitrogen atom to which they are bonded may form a ring, and the ring may be substituted, R$^6$ represents a hydrogen, an optionally substituted lower alkyl, an optionally substituted arylalkyl or an optionally substituted heteroarylalkyl and R$^{14}$, R$^{15}$ and R$^{16}$ are the same as or different from each other and represent a hydrogen, a halogen, an optionally substituted lower alkyl or an optionally substituted lower alkoxy, or two of R$^{14}$, R$^{15}$ and R$^{16}$ bonded to carbon atoms adjacent to each other may form methylenedioxy or ethylenedioxy.

9. The remedy as set forth in claim 1, wherein the compound is one selected from among the following compounds:

1) 1-chloro-4-(3-chloro-4-methoxybenzyl)amino-6-cyano-phthalazine;

2) 1-chloro-6-cyano-4-(2-methoxyethyl) aminophthalazine;
3) 1-chloro-4-(3-chloro-4-methoxyanilino)-6-cyanophthalazine;
4) 1-chloro-6-cyano-4-(4-methoxybenzyl) aminophthalazine;
5) 1-chloro-4-(α-methyl-3-chloro-4-methoxybenzyl) amino-6-cyanophthalazine;
6) 1-chloro-4-(3-chloro-4-ethoxybenzyl)amino-6-cyanophthalazine;
7) 1-chloro-4-(3-chloro-4-methoxybenzyl)amino-6-trifluorophthalazine;
8) 1-chloro-4-(3-chloro-4-methoxybenzyl)amino-6-(N,N-dimethylsulfamoyl)phthalazine;
9) 1-(3-chloro-4-methoxybenzyl)amino-4,6,7-trichlorophthalazine;
10) 1-(3-chloro-4-methoxybenzyl)amino-4,6-dichlorophthalazine;
11) 4-chloro-1-(3-chloro-4-methoxybenzyl)amino-6-nitro-phthalazine;
12) 4-chloro-1-[3-chloro-4-(4-methoxybenzyloxy)-benzyl]amino-6-cyanophthalazine;
13) 4-chloro-1-(3-chloro-4-ethoxybenzyl)amino-6-cyano-phthalazine;
14) 8-(3-chloro-4-methoxybenzyl)amino-5-(4-hydroxypiperidino)pyrido[2,3-d]pyridazine;
15) 4-(3-chloro-4-methoxybenzyl)amino-6-cyano-1-(4-hydroxypiperidino)phthalazine;
16) 1-(4-carbamoylpiperidino)-4-(3-chloro-4-methoxybenzyl)amino-6-cyanophthalazine;
17) 6-chloro-4-(3-chloro-4-methoxybenzyl)amino-1-(3-hydroxypyrrolidino)phthalazine;
18) 6-chloro-1-(4-ethoxycarbonylpiperidino)-4-(3,4-methylenedioxybenzyl)aminophthalazine;
19) 4-(3-chloro-4-methoxybenzyl)amino-1-[4-(2-hydroxyethyl)piperazin-1-yl]-6-nitrophthalazine;
20) 1-(3-chloro-4-methoxybenzyl)amino-6,7-dichloro-4-(4-ethoxycarbonylpiperidino)phthalazine;
21) 4-[4-(3-chloro-4-methoxybenzyl)amino-6-cyanophthalazin-1-yl]thiomorpholine 1,1-dioxide;
22) 4-(3-chloro-4-methoxybenzyl)amino-6-cyano-1-[4-(methanesulfonamido)piperidino]phthalazine;
23) 4-(3-chloro-4-methoxybenzyl)amino-6-cyano-[(trans-4-hydroxy-1-cyclohexyl)amino]phthalazine;
24) 4-(3-chloro-4-methoxybenzyl)amino-6-cyano-1-piperidinophthalazine;
25) 4-(3-chloro-4-methoxybenzyl)amino-6-cyano-1-(thio-morpholino)phthalazine;
26) 4-(3-chloro-4-methoxyanilino)-6-cyano-1-(4-hydroxy-piperidino)phthalazine; and
27) 4-[2-(3-chloro-4-methoxyphenyl)ethylamino-6-cyano-1-(4-hydroxypiperidino)phthalazine.

10. A method for treating female sexual dysfunction, dysmenorrhea or premature birth which comprises administering an effective amount of a fused pyridazine compound represented by the following formula (I) or a pharmacologically acceptable salt thereof to a patient in need thereof:

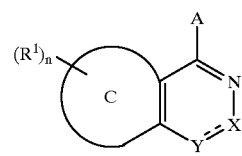

(I)

wherein the ring C represents an unsaturated 5 or 6 membered ring optionally having one heteroatom;
  n is 0 or an integer of from 1 to 4;
  $R^1$ represents a halogen, an optionally substituted lower alkyl, an optionally substituted lower alkoxy, an optionally substituted cycloalkyl, a nitro, a cyano, a group represented by the formula $-NR^2R^3$,
    wherein $R^2$ and $R^3$ are the same as or different from each other and represent a hydrogen, an optionally substituted lower alkyl, an acyl, an optionally substituted arylalkyl or an optionally substituted heteroarylalkyl, or $R^2$ and $R^3$ together with the nitrogen atom to which they are bonded may form a ring, and the ring may be substituted,
  a group represented by the formula $-O-R^9$,
    wherein $R^9$ represents a hydrogen, an optionally substituted lower alkyl, acyl, an optionally substituted arylalkyl or an optionally substituted heteroarylalkyl,
  a group represented by the formula $-S-R^{10}$,
    wherein $R^{10}$ represents a hydrogen, an optionally substituted lower alkyl, acyl, an optionally substituted arylalkyl or an optionally substituted heteroarylalkyl, a group represented by the formula:

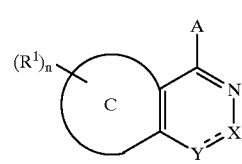

(I)

wherein $R^{11}$ represents a hydrogen, a lower alkyl or an amino; and m is 0 or an integer of 1 or 2, or an optionally protected carboxy, provided that when n is 2 to 4, then $R^1$s may independently represent the above substituents;
A represents a hydrogen, a halogen, a group represented by the formula $-NR^4R^5$,
  wherein $R^4$ and $R^5$ are the same as or different from each other and represent a hydrogen, an optionally substituted lower alkyl, an acyl, an optionally substituted arylalkyl or an optionally substituted heteroarylalkyl, or $R^4$ and $R^5$ together with the nitrogen atom to which they are bonded may form a ring, and the ring may be substituted,
an optionally substituted aryl, an optionally substituted heteroaryl, an optionally substituted arylalkyl or an optionally substituted heteroarylalkyl;
X represents a group represented by the formula $-NR^6-$, wherein $R^6$ represents a hydrogen, an optionally substituted lower alkyl, an optionally substituted arylalkyl or an optionally substituted heteroarylalkyl or a group represented by the formula $-N=$;
Y represents a group represented by the formula $-CO-$ or $-C(B)=$, wherein B represents a hydrogen, a halogen, a group represented by the formula $-NR^7R^8$, wherein R⁷ and R⁸ are the same as or different from each other and represent a hydrogen, an optionally substituted lower alkyl, an acyl, an optionally substituted arylalkyl or an optionally substituted heteroarylalkyl, or R⁷ and R⁸ together with the nitrogen atom to which they are bonded may form a ring, and the ring may be substituted, a group represented by the formula —O—R¹², wherein R¹² represents a hydrogen, an optionally substituted lower alkyl, an acyl, an optionally substituted arylalkyl or an optionally substituted heteroarylalkyl, a group represented by the formula —S—R¹³, wherein R¹³ represents a hydrogen, an optionally substituted lower alkyl, an acyl, an optionally substituted arylalkyl or an optionally substituted heteroarylalkyl, an optionally substituted aryl, an optionally substituted heteroaryl, an optionally substituted arylalkyl or an optionally substituted heteroarylalkyl; and ----- represents a double or single bond;

provided that when C is a benzene ring, then the case where n is 0 is excluded.

11. A medicinal composition which comprises a therapeutically effective dose of the fused pyridazine compound as set forth in claim 1 or a pharmacologically acceptable salt thereof and pharmacologically acceptable carriers.

12. A method for treating erectile dysfunction, female sexual dysfunction, dysmenorrhea or premature birth which comprises administering a theraperutically effective dose of the fused pyridazine compound as set forth in claim 1 or a pharmacologically acceptable salt thereof to a patient with erectile dysfunction, female sexual dysfunction or dysmenorrhea or a patient giving premature birth.

* * * * *